US009024099B2

(12) United States Patent
Moser et al.

(10) Patent No.: US 9,024,099 B2
(45) Date of Patent: *May 5, 2015

(54) CO-CURRENT CATALYST FLOW WITH FEED FOR FRACTIONATED FEED RECOMBINED AND SENT TO HIGH TEMPERATURE REFORMING REACTORS

(75) Inventors: Mark D. Moser, Elk Grove Village, IL (US); Kurt M. VandenBussche, Lake in the Hills, IL (US); David A. Wegerer, Lisle, IL (US); Gregory J. Gajda, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 25 days.

This patent is subject to a terminal disclaimer.

(21) Appl. No.: 13/327,200

(22) Filed: Dec. 15, 2011

(65) Prior Publication Data
US 2013/0158318 A1 Jun. 20, 2013

(51) Int. Cl.
C10G 35/04 (2006.01)
C07C 5/02 (2006.01)
C07C 5/42 (2006.01)
C10G 59/02 (2006.01)
C10G 59/06 (2006.01)
C10G 69/08 (2006.01)

(52) U.S. Cl.
CPC . C07C 5/42 (2013.01); C10G 35/04 (2013.01); C10G 59/02 (2013.01); C10G 59/06 (2013.01); C10G 69/08 (2013.01)

(58) Field of Classification Search
CPC .............. C07C 5/00; C07C 5/02; C07C 5/03; C07C 5/32; C07C 5/321; C07C 5/324; C07C 5/325; C07C 4/00; C07C 4/02; C07C 4/04; C07C 4/06; C10G 35/00; C10G 35/02; C10G 35/04; C10G 35/06; C10G 35/085; C10G 35/09
USPC ......... 585/312, 251, 300–304, 315, 319, 322, 585/407, 430, 800, 804, 805
See application file for complete search history.

(56) References Cited

U.S. PATENT DOCUMENTS

| 2,620,314 | A |   | 12/1952 | Hoekstra |
| 3,647,680 | A | * | 3/1972 | Greenwood ..................... 208/65 |
| 3,951,868 | A |   | 4/1976 | Wilhelm |
| 4,401,554 | A | * | 8/1983 | Choi et al. ...................... 208/64 |
| 5,885,439 | A |   | 3/1999 | Glover |
| 5,935,415 | A | * | 8/1999 | Haizmann et al. .............. 208/64 |
| 6,004,452 | A | * | 12/1999 | Ash et al. ......................... 208/80 |
| 7,534,737 | B2 |  | 5/2009 | Gajda |
| 2007/0299289 | A1 | * | 12/2007 | Bresler et al. .................. 585/323 |

OTHER PUBLICATIONS

Sinnott, R.K. (2005). Coulson and Richardson's Chemical Engineering vol. 6—Chemical Engineering Design (4th Edition) . . . Elsevier.*

(Continued)

Primary Examiner — In Suk Bullock
Assistant Examiner — Philip Louie

(57) ABSTRACT

A process is presented for the increasing the yields of aromatics from reforming a hydrocarbon feedstream. The process includes splitting a naphtha feedstream into a light hydrocarbon stream, and a heavier stream having a relatively rich concentration of naphthenes. The heavy stream is reformed to convert the naphthenes to aromatics and the resulting product stream is further reformed with the light hydrocarbon stream to increase the aromatics yields. The catalyst is passed through the reactors in a sequential manner.

10 Claims, 2 Drawing Sheets

(56) References Cited

OTHER PUBLICATIONS

U.S. Appl. No. 13/327,164, filed Dec. 15, 2011, Moser et al.
U.S. Appl. No. 13/327,143, filed Dec. 15, 2011, Moser et al.
U.S. Appl. No. 13/327,212, filed Dec. 15, 2011, Moser et al.
U.S. Appl. No. 13/327,220, filed Dec. 15, 2011, Moser et al.
U.S. Appl. No. 13/327,185, filed Dec. 15, 2011, Serban et al.
U.S. Appl. No. 13/327,178, filed Dec. 15, 2011, Serban et al.
U.S. Appl. No. 13/327,170, filed Dec. 15, 2011, Serban et al.
U.S. Appl. No. 13/327,192, filed Dec. 15, 2011, Serban et al.
U.S. Appl. No. 13/416,513, filed Mar. 9, 2012, Serban.
U.S. Appl. No. 13/416,702, filed Mar. 9, 2012, Gajda.
U.S. Appl. No. 13/417,181, filed Mar. 9, 2012, Gajda.
U.S. Appl. No. 13/417,200, filed Mar. 9, 2012, Wegerer.
U.S. Appl. No. 13/417,202, filed Mar. 9, 2012, Gajda.
U.S. Appl. No. 13/417,203, filed Mar. 10, 2012, Gajda.
U.S. Appl. No. 13/440,487, filed Apr. 5, 2012, Moser.
U.S. Appl. No. 13/440,527, filed Apr. 5, 2012, Moser.
U.S. Appl. No. 13/440,381, filed Apr. 5, 2012, Moser.
U.S. Appl. No. 13/428,005, filed Mar. 23, 2012, Serban.
U.S. Appl. No. 13/416,604, filed Mar. 9, 2012, Serban.
U.S. Appl. No. 13/416,577, filed Mar. 9, 2012, Negiz.
PCT International Preliminary Report on Patentability for PCT/US2012/054972, mailing date Jun. 26, 2014.

* cited by examiner

CO-CURRENT CATALYST FLOW WITH FEED FOR FRACTIONATED FEED RECOMBINED AND SENT TO HIGH TEMPERATURE REFORMING REACTORS

FIELD OF THE INVENTION

The present invention relates to the process of enhancing the production of aromatic compounds. In particular the improvement and enhancement of aromatic compounds such as benzene, toluene and xylenes from a naphtha feedstream.

BACKGROUND OF THE INVENTION

The reforming of petroleum raw materials is an important process for producing useful products. One important process is the separation and upgrading of hydrocarbons for a motor fuel, such as producing a naphtha feedstream and upgrading the octane value of the naphtha in the production of gasoline. However, hydrocarbon feedstreams from a raw petroleum source include the production of useful chemical precursors for use in the production of plastics, detergents and other products.

The upgrading of gasoline is an important process, and improvements for the conversion of naphtha feedstreams to increase the octane number have been presented in U.S. Pat. Nos. 3,729,409, 3,753,891, 3,767,568, 4,839,024, 4,882,040 and 5,242,576. These processes involve a variety of means to enhance octane number, and particularly for enhancing the aromatic content of gasoline.

In addition, the production of aromatics is important. Aromatics, such as benzene, are used in plastics production and the production of detergents. Increasing the yields of aromatic compounds from hydrocarbons streams increases the return, as lower value hydrocarbons are converted to higher value aromatics.

Processes include splitting feeds and operating several reformers using different catalysts, such as a monometallic catalyst or a non-acidic catalyst for lower boiling point hydrocarbons and bi-metallic catalysts for higher boiling point hydrocarbons. Other improvements include new catalysts, as presented in U.S. Pat. Nos. 4,677,094, 6,809,061 and 7,799,729. However, there are limits to the methods and catalysts presented in these patents, and which can entail significant increases in costs.

The increased demand generates pressure to improve the processes for increasing the production of aromatics.

SUMMARY OF THE INVENTION

The invention comprises controlling the process and catalyst flow to improve the yields of aromatics from a naphtha feedstock. The naphtha feedstock is split into a light stream having C7 and lighter hydrocarbons and a heavy stream having C8 and heavier hydrocarbons and naphthenes. The heavy stream is passed through a first reactor system to convert the naphthenes to aromatics, and generate a first effluent stream. The light stream and the first effluent stream are passed to a second reactor system for converting C6 and C7 paraffins to aromatics. The process includes passing a reforming catalyst through the first reactor system to generate a first catalyst effluent stream. The first catalyst effluent stream is passed to the second reactor system and flows through the reactors in the second reactor system. The second reactor system is held at a substantially isothermal condition to maximize the conversion to benzene and toluene.

Other objects, advantages and applications of the present invention will become apparent to those skilled in the art from the following drawings and detailed description of the invention.

DETAILED DESCRIPTION OF THE INVENTION

A process is presented for addressing the need to increase the yields of benzene, toluene and xylenes from a hydrocarbon feedstream. The hydrocarbon feedstream is usually a full boiling range naphtha feedstream and the naphtha feedstream is reformed to generate C6 to C10 aromatics. The reformation process involves a catalytic reactor to selectively convert naphthenes and paraffins to aromatic compounds. In general, catalytic reforming generates unwanted byproducts, which include methane, ethane and to a lesser degree propanes and butanes. These are low value products and processes that reduce the formation of these byproducts and increase the amount of aromatics improves the economics of the reforming process.

Catalytic reforming of hydrocarbons proceeds through numerous chemical reaction pathways. The reforming reaction rates vary with temperature, and the Arrhenius equation captures the relationship between reaction rate (k) and reaction temperature (T), where each reaction has an activation energy (Ea). The equation becomes:

$$k = A * \exp(-Ea/RT), \text{ where } A \text{ is the individual reaction rate coefficient.}$$

Reactions with different activation energies will be affected differently by the reaction temperature and changes in the reaction temperature. In the case of catalytic reforming there are numerous parallel reaction pathways, or competing reaction pathways. With different activation energies, it is possible to manipulate the conversion rates to desired products by controlling the reaction temperatures. However, since there are a large number of parallel reactions, the practical control is limited to classes, or types, of chemical compounds being reformed, and the control is over the ability to sufficiently segregate the classes of compounds. In the case of naphtha, the catalytic reforming process is endothermic overall. For an adiabatic reaction system, there is a substantial temperature decrease and this adversely affects the rates of conversion. By segregating the most endothermic compounds, and reforming the more endothermic compounds, the temperatures of the reactions are more easily controlled, and the yields can be increased. This also has a benefit of reducing the selectivity of undesired side products.

Figure 1:
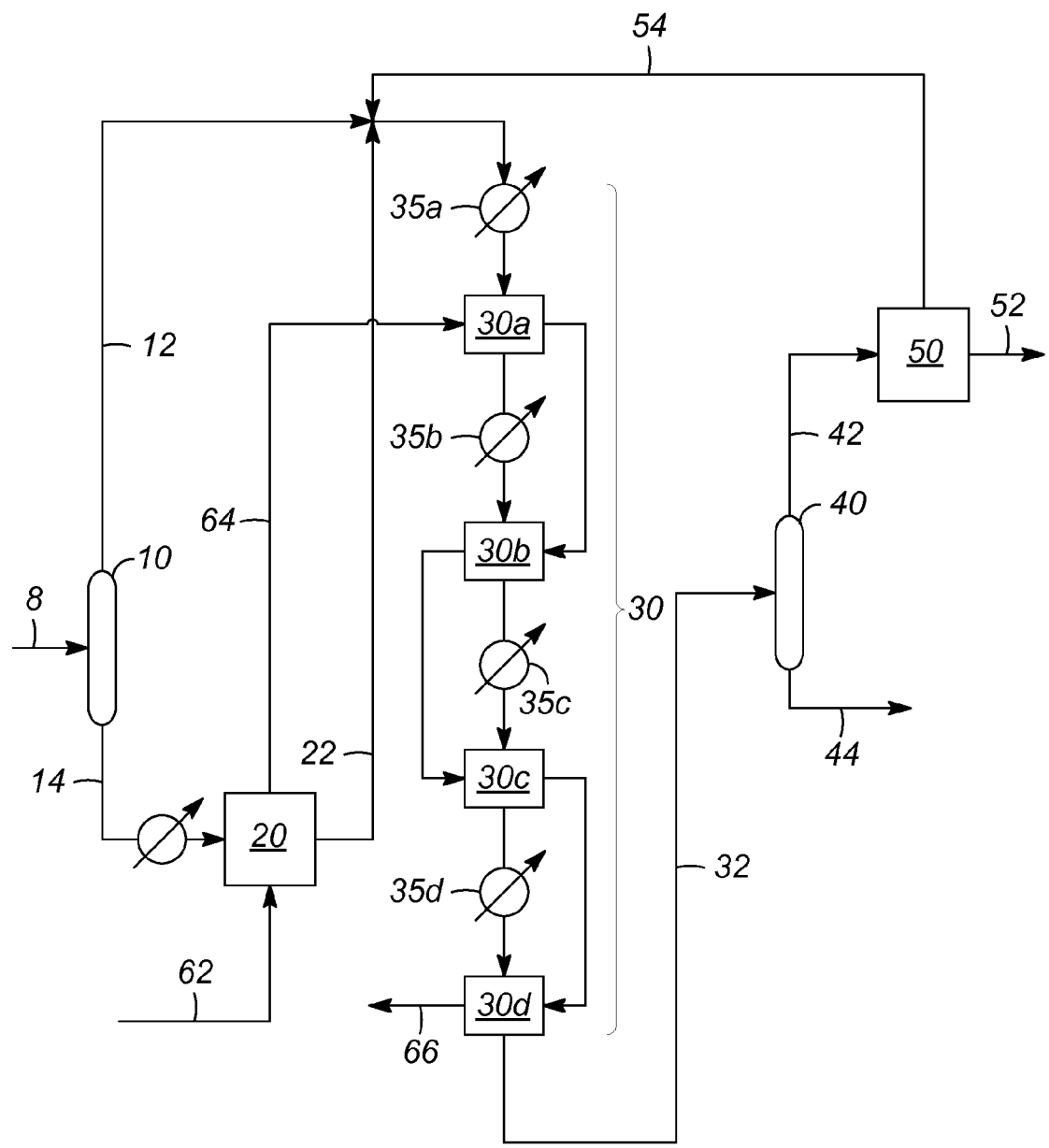
FIG. 1 shows the flow scheme for parallel flow with split feed and recombination for secondary reforming.

Improving the catalysts has been the main focus of improving the reforming process, however, modifying the process using non-obvious rearrangements can yield unexpected results. The present invention for reforming a hydrocarbon feedstream is shown in FIG. 1. The process includes passing the feedstream 8 to a fractionation system 10 to generate an overhead stream 12 and a bottoms stream 14. The bottoms stream 14 is passed to a first reforming reactor system 20, and is operated at a first set of reaction conditions to generate a first reactor system effluent 22. The first reactor effluent 22 has an increased aromatics content.

The first reactor effluent 22 and the overhead stream 12 are passed to a second reforming reactor system 30. The second reforming reactor system 30 generates a second effluent stream 32 rich in aromatics. The second effluent stream 32 is passed to a reformate splitter 40 to generate a reformate overhead stream 42 comprising C7 and lighter aromatics, and a reformate bottoms stream 44 comprising C8 and heavier aromatics. The reformate overhead stream 42 is passed to an aromatics recovery unit 50 to generate an aromatics product stream 52 and a raffinate stream 54 comprising non-aromatic hydrocarbons. The raffinate stream 54 can be passed back to the second reactor system 30 for further conversion of the hydrocarbons to aromatics.

In a preferred embodiment, the overhead stream 12 comprises n-hexane and lighter components. The bottoms stream 14 comprises cyclohexane and heavier components. The naphthenes in the bottoms stream 14 are processed in the first reforming reactor system 20 to process the components that have the highest endothermicity. This leads to lower energy usage to maintain the inlet temperatures in the second reactor system 30. The first reforming reactor system 20 will have an inlet temperature less than 540° C., for the conversion of the naphthenes to aromatics. The second reforming reactor system 30 will preferably have the inlet temperatures greater than or equal to or near 540° C. Each reactor in the reactor systems will have a heating unit to bring the temperature of the reactor feed to the desired reaction temperatures.

The process includes operating the second reactor system 30 in an operating regime to minimize the temperature changes within the reactor system 30. The reforming process is endothermic, and the reactions drive the temperature down in the reactors relative to the inlet temperature. The second reactor system 30 can comprise a plurality of reactors with inter-reactor heaters. In FIG. 1, the plurality of reactors are shown by 30a, 30b, 30c and 30d, with the heaters shown by 35a, 35b, 35c and 35d.

The catalyst used in this process is passed through the various reactors 20, 30. Catalyst 62 is preferably passed through the first reactor system 20 to generate a first reactor system catalyst effluent stream 64. The first catalyst effluent stream is then passed to the second reactor system 30, where the catalyst is subject to a greater operating temperature. The catalyst passes through each reforming reactor in the second reactor system 30, and is returned as a second catalyst effluent stream 66 to a regenerator.

Figure 2:
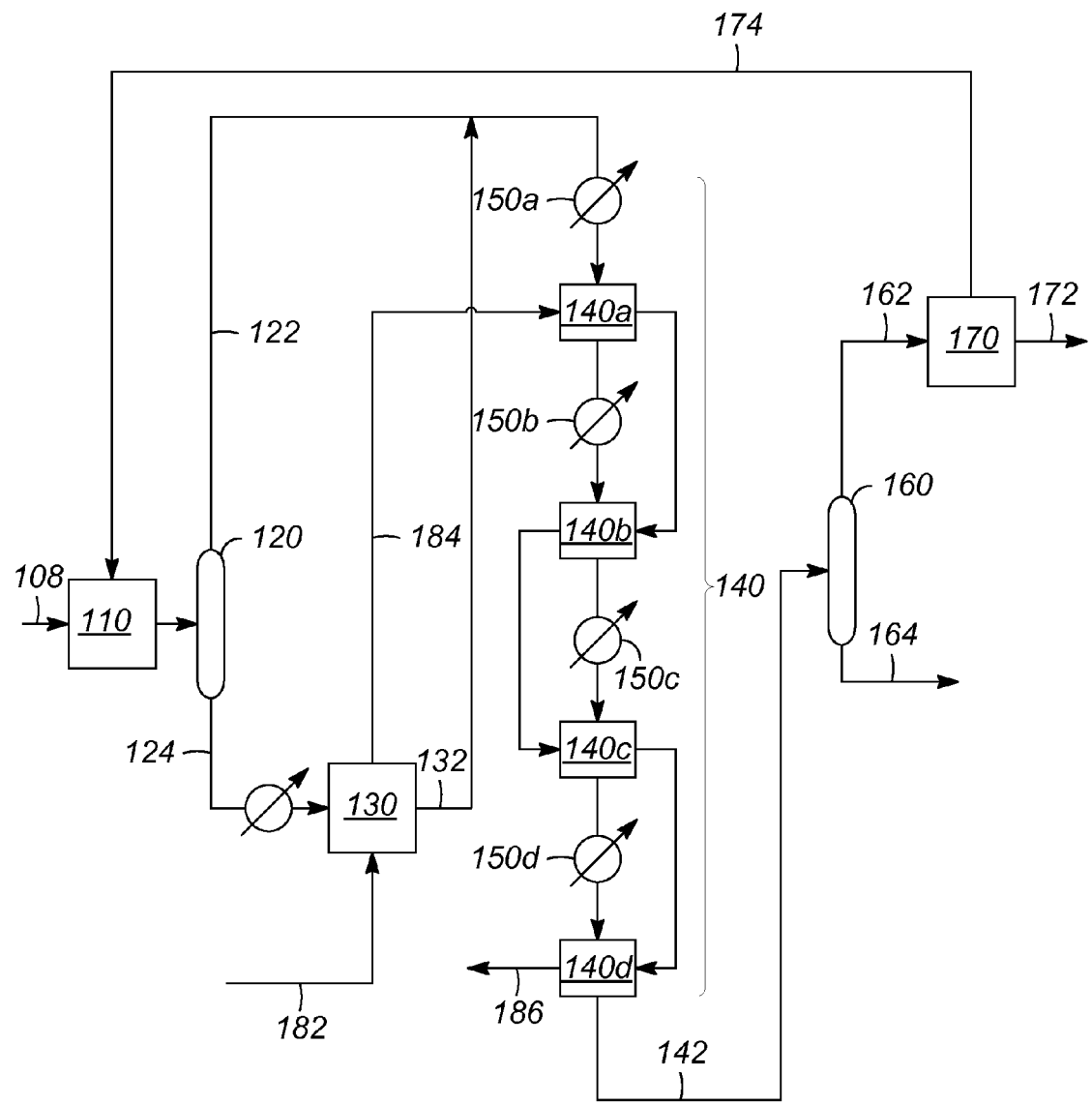
FIG. 2 shows the flow scheme for a parallel flow with naphtha hydrotreatment of the feed and recycle.

In a second embodiment, as shown in FIG. 2, comprises passing a hydrocarbon feedstream 108 to a hydrotreating unit 110 to generate a treated hydrocarbon feed 112. With a preferred hydrocarbon feed, the hydrotreating unit 110 is a naphtha hydrotreater. The treated feed 112 is passed to a fractionation system 120 to generate a light overhead stream 122 comprising n-hexane and lighter hydrocarbons. The fractionation system 120 also generates a bottoms stream 124 comprising cyclohexane and heavier components. The bottoms stream 124 is passed to a first reactor system 130 to generate a first effluent stream 132 having increased aromatics content. The bottoms stream 122 is heated to an inlet reaction temperature for the catalytic reforming reaction in the reactor system 130. The overhead stream 122 and the first effluent stream 132 are passed to a second reactor system 140. The second reactor system 140 includes a plurality of reactor units 140a, b, c, d and reactor feed heaters 150a, b, c, d, where the feed stream to each reactor is heated to a desired inlet temperature. The second reactor system 140 is sized and designed to minimize the temperature drops within the reactors due to the endothermic nature of the reforming reactions.

The second reactor system 140 generates a second effluent stream 142 and is passed to a reformate splitter 160. The reformate splitter 160 generates a reformate overhead stream 162 having C7 and lighter aromatic compounds, and a reformate bottoms stream 164 comprising C8 and heavier hydrocarbon compounds. The reformate overhead stream 162 is passed to an aromatics recovery unit 170 to generate an aromatics product stream 172 comprising benzene and toluene. The aromatics recovery unit 170 also generates a raffinate stream 174 comprising non-aromatic hydrocarbons. A portion of the raffinate stream 174 can be returned into the reactor system for converting the hydrocarbons to aromatics. The raffinate stream 174 is passed to the hydrotreating unit 110 to process and remove residual sulfur picked up from the aromatics recovery unit 170.

A catalyst stream 182 from a regenerator is passed to the first reactor system 130 to generate a first reactor catalyst effluent stream 184. The first reactor catalyst effluent stream 184 passes to the second reactor system 140 where the catalyst passes through the plurality of reactors and generates a second reactor system catalyst effluent stream 186. The second reactor catalyst effluent stream 186 is returned to the regenerator.

The aromatics recovery unit 170 can comprise different methods of separating aromatics from a hydrocarbon stream. One industry standard is the Sulfolane™ process, which is an extractive distillation process utilizing sulfolane to facilitate high purity extraction of aromatics. The Sulfolane™ process is well known to those skilled in the art.

The first reactor system 130 is operated for the conversion of naphthenes to aromatics, and is operated at a lower temperature than the second reactor system 140. The first reactor system 130 will experience greater temperature drops due to the higher relative concentration of endothermic compounds, such as the naphthenes, converted to aromatics before passing the first effluent stream 132 on to the second reactor system 140. The first reactor system 130 includes an inlet temperature less than 540° C., and the second reactor system includes heaters to raise the inlet temperature of the reactor feed streams to at least 540° C.

The catalyst used is a reforming catalyst, and the process is a moving bed process where the catalyst is cycled through the reactors and then regenerated. The catalyst as it passes through the reactors is partially deactivated, and the process yields and selectivities can be maintained through raising the temperature of the reaction. The process therefore passes catalyst from a regenerator to the first reactor system, and generates a first catalyst effluent stream. The first catalyst effluent stream is passed to the second reactor system and generates a second catalyst effluent stream. The second catalyst effluent stream is passed to the regenerator to return the catalyst to a regenerated state.

When the second reactor system comprises a plurality of reactors, the catalyst can be passed sequentially through the reactors in a series relationship. The catalyst enters the first reactor in the series and sequentially passes through each reactor, with the catalyst reheated upon leaving a reactor and before entering the subsequent reactor to the reaction inlet temperatures. The catalyst exiting the final reactor in the series is passed to the regenerator.

The isothermal reactor system, or second reactor system, utilizes a reforming catalyst and is operated at a temperature between 520° C. and 600° C., with a preferred operating temperature between 540° C. and 560° C., with the reaction conditions controlled to maintain the isothermal reactions at or near 540° C. A plurality of reactors with inter-reactor heaters provides for setting the reaction inlet temperatures to a narrow range, and multiple, smaller reactors allow for limiting the residence time and therefore limiting the temperature variation across the reactor system 40. The process of reforming also includes a space velocity between 0.6 hr$^{-1}$ and 10 hr$^{-1}$. Preferably the space velocity is between 0.6 hr$^{-1}$ and 8 hr$^{-1}$, and more preferably, the space velocity is between 0.6 hr$^{-1}$ and 5 hr$^{-1}$.

Reforming catalysts generally comprise a metal on a support. The support can include a porous material, such as an inorganic oxide or a molecular sieve, and a binder with a weight ratio from 1:99 to 99:1. The weight ratio is preferably from about 1:9 to about 9:1. Inorganic oxides used for support include, but are not limited to, alumina, magnesia, titania, zirconia, chromia, zinc oxide, thoria, boria, ceramic, porcelain, bauxite, silica, silica-alumina, silicon carbide, clays, crystalline zeolitic aluminasilicates, and mixtures thereof. Porous materials and binders are known in the art and are not presented in detail here. The metals preferably are one or more Group VIII noble metals, and include platinum, iridium, rhodium, and palladium. Typically, the catalyst contains an amount of the metal from about 0.01% to about 2% by weight, based on the total weight of the catalyst. The catalyst can also include a promoter element from Group IIIA or Group IVA. These metals include gallium, germanium, indium, tin, thallium and lead.

The first reforming reactor system uses the same catalyst, but is operated at a lower temperature and allows for greater temperature swings within the reactor.

An alternative arrangement is for the catalyst to be passed in parallel to each of the reactors in the second reactor system. This provides for fresher catalyst as the process flow stream passes through each reactor in a series arrangement to increase the yields of aromatics. The catalyst, after passing through the reactors, is then passed to the regenerator.

When the first reactor system comprises a plurality of reactors, the catalyst from the regenerator can be passed to the first reactor in the first reactor system with the catalyst flowing through the subsequent reactors in a series arrangement. The catalyst is not heated before entering each reactor. Optionally, the catalyst can be reheated to the reactor inlet temperatures.

An alternate arrangement is for the catalyst from the regenerator to be split and passed in a parallel arrangement to the plurality of reactors in the first reactor system, with each reactor generating a first catalyst effluent stream. The catalyst in the first catalyst effluent streams are combined and routed to the second reactors in the second reactor system.

TABLE 1

Example of Yield Benefit Via Split Feed Series

| Products | Base Case C6 Split Feed 0% Raffinate Recycle 3 - Isothermal RxRs 55% P6 Conversion (Kg/hr) | Paraffin Recycle Case C6 Split Feed 75% C6+ Raffinate Recycle 3 - Isothermal RxRs 55% P6 Conversion (Kg/hr) | % Change (Paraffin Recycle - Base) |
|---|---|---|---|
| H2 | 8035.0 | 8184.0 | 1.9% |
| C1-C2 | 8053.5 | 6889.7 | -14.5% |
| C3-C4 | 16939.9 | 14847.7 | -12.4% |
| Light Gasoline | 8326.0 | 8774.8 | 5.4% |
| Raffinate | 10060.1 | 11716.0 | 16.5% |
| Benzene | 13431.1 | 13445.5 | 0.1% |
| Toluene | 41747.4 | 41828.8 | 0.2% |
| PX | 9010.3 | 8961.9 | -0.5% |
| A8 (excluding PX) | 39452.4 | 39228.9 | -0.6% |
| A9 | 29372.7 | 30019.2 | 2.2% |
| A10 | 5810.3 | 5978.8 | 2.9% |
| Total A6-A10 | 138824.3 | 139463.1 | 0.5% |

The process was divided into two reaction zones. The first reaction zone performed reformation of more highly endothermic compounds, such as naphthenes, where the temperature dropped more. The second reaction zone was controlled to simulate an isothermal system, with the temperature drops within the reactions in the second reaction zone reduced due to the reduction in the amount of highly endothermic compounds. The results from simulations of the reactions show an increase in the desired benzene and toluene, with a reduction in the amounts of light hydrocarbons in the C1-C4 range.

The process shows the separation of the feed into highly endothermic compounds and unconverted paraffin compounds. The highly endothermic compounds were passed to the non-isothermal reactor system, or the first reactor system, and the less endothermic compounds were passed to the substantially isothermal reactor system, or second reactor system. The process included passing the first reactor system effluent with unconverted paraffins to the isothermal reactor system, and the recycling of unconverted paraffins to the reforming reactors.

Therefore, increases can be achieved through innovative flow schemes that allow for process control of the reactions. While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for reforming a hydrocarbon feedstream, comprising:
    passing the feedstream to a fractionation system to create a first overhead stream comprising n-hexane and lighter hydrocarbons, and a first bottoms stream comprising cyclohexane and heavier hydrocarbons;
    passing the first bottoms stream to a first reformer reactor, operated at a first set of reforming conditions, wherein the first set of reforming conditions include a temperature less than 540° C., to generate a first reactor effluent having an increased aromatic content;
    passing the first overhead stream and the first reactor effluent to a second reforming reactor system operated at a second set of reforming conditions, wherein the second set of reforming conditions include a temperature greater than or equal to 540° C., thereby generating a second effluent stream;
    passing a first regenerated catalyst stream to the first reformer reactor and generating a first reformer catalyst effluent stream;

passing a second catalyst stream to the second reformer reactor system and generating a second reformer catalyst effluent stream;

passing the second effluent stream to a reformate splitter to generate a second overhead stream comprising C7 and lighter aromatics, and a second bottoms stream comprising C8 and heavier aromatics; and passing the second overhead stream to an aromatics recovery unit, thereby generating an aromatics product stream comprising benzene and toluene, and a raffinate stream comprising non-aromatic hydrocarbons;

wherein the catalyst for all the reforming reactors is the same.

2. The process of claim 1 further comprising:

passing the hydrocarbon feedstream to a hydrotreating unit to create a treated hydrocarbon feedstream; and passing the treated hydrocarbon feedstream to the fractionation system.

3. The process of claim 2 further comprising passing a portion of the raffinate stream to the hydrotreating unit.

4. The process of claim 1 wherein the second reforming reactor system comprises a plurality of reactors and inter-reactor heaters.

5. The process of claim 1 wherein the hydrocarbon feedstream is a full boiling range naphtha feedstream.

6. The process of claim 1 wherein the second catalyst stream is the first reformer catalyst effluent stream.

7. The process of claim 4 wherein the second catalyst stream is passed through the plurality of reactors in a series flow, with inter-reactor heaters to reheat the catalyst.

8. A process for reforming a hydrocarbon feedstream, comprising:

passing the hydrocarbon feedstream to a hydrotreating unit to create a hydrotreated hydrocarbon feedstream; and passing the hydrotreated feedstream to a fractionation system to create a first overhead stream comprising n-hexane and lighter hydrocarbons, and a first bottoms stream comprising cyclohexane and heavier hydrocarbons;

passing the first bottoms stream to a first reformer reactor, operated at a first set of reforming conditions, wherein the first set of reforming conditions include a temperature less than 540° C., to generate a first reactor effluent having an increased aromatic content;

passing the first overhead stream and the first reactor effluent to a second reforming reactor system operated at a second set of reforming conditions, wherein the second set of reforming conditions include a temperature greater than or equal to 540° C., and wherein the second reforming reactor system comprises a plurality of reactors and inter-reactor heaters, thereby generating a second effluent stream;

passing a regenerated catalyst stream to the first reactor, thereby generating a first reactor catalyst effluent stream;

passing the first reactor catalyst effluent stream to the second reactor system, thereby generating a second reactor catalyst effluent stream;

passing the second reactor catalyst effluent stream to a regenerator, thereby creating a regenerated catalyst stream;

passing the second effluent stream to a reformate splitter to generate a second overhead stream comprising C7 and lighter aromatics, and a second bottoms stream comprising C8 and heavier aromatics; and passing the second overhead stream to an aromatics recovery unit, thereby generating an aromatics product stream comprising benzene and toluene, and a raffinate stream comprising non-aromatic hydrocarbons;

wherein the catalyst for all the reforming reactors is the same.

9. The process of claim 8 wherein the first catalyst effluent passed to the second reactor system flows between the plurality of reactors and inter-reactor heaters in the same direction as the first reactor effluent stream.

10. The process of claim 8 further comprising passing a portion of the raffinate stream to the hydrotreating unit.

* * * * *